(12) United States Patent
Hsieh

(10) Patent No.: US 8,548,568 B2
(45) Date of Patent: Oct. 1, 2013

(54) METHODS AND APPARATUS FOR MOTION COMPENSATION

(75) Inventor: Jiang Hsieh, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 1384 days.

(21) Appl. No.: 11/517,964

(22) Filed: Sep. 8, 2006

(65) Prior Publication Data

US 2008/0086052 A1    Apr. 10, 2008

(51) Int. Cl.
*A61B 5/05* (2006.01)

(52) U.S. Cl.
USPC .......................................................... 600/427

(58) Field of Classification Search
USPC .......................................... 600/427; 382/128
See application file for complete search history.

(56) References Cited

U.S. PATENT DOCUMENTS

| | | | |
|---|---|---|---|
| 5,521,644 A | 5/1996 | Sezan et al. | 348/452 |
| 5,779,641 A * | 7/1998 | Hatfield et al. | 600/443 |
| 6,487,304 B1 | 11/2002 | Szeliski | 382/107 |
| 2001/0009974 A1* | 7/2001 | Reisfeld | 600/407 |
| 2004/0044282 A1* | 3/2004 | Mixon et al. | 600/427 |
| 2005/0002550 A1* | 1/2005 | Jabri et al. | 382/131 |
| 2005/0226527 A1* | 10/2005 | Weese et al. | 382/275 |
| 2005/0232514 A1* | 10/2005 | Chen | 382/298 |
| 2005/0238253 A1* | 10/2005 | Behrenbruch et al. | 382/294 |
| 2005/0243203 A1 | 11/2005 | Swan | 348/448 |
| 2006/0018439 A1* | 1/2006 | Tang et al. | 378/210 |
| 2006/0078085 A1 | 4/2006 | Zanker | 378/57 |
| 2006/0173304 A1* | 8/2006 | Wang | 600/437 |
| 2007/0183639 A1* | 8/2007 | Kohler et al. | 382/131 |

OTHER PUBLICATIONS

C. J. Ritchie, J. D. Godwin, C. R. Crawford, W. Stanford, H. Anno, Y. Kim, "Minimum Scan Speeds for Suppression of Motion Artifacts in CT," Radiology 185(1), pp. 37-42, 1992.

* cited by examiner

*Primary Examiner* — Tse Chen
*Assistant Examiner* — Hien Nguyen
(74) *Attorney, Agent, or Firm* — Ziolkowski Patent Solutions Group, SC

(57) ABSTRACT

A method includes fitting a motion map from a first imaging modality with a first FOV to a second imaging modality different from the first with a second FOV sized differently than the first FOV.

19 Claims, 3 Drawing Sheets

METHODS AND APPARATUS FOR MOTION COMPENSATION

BACKGROUND OF THE INVENTION

This invention relates generally to methods and apparatus for computed tomography (CT), and more particularly to methods and apparatus for motion compensation in CT.

Motion compensation is a major issue in computed tomography (CT). This is mainly due to the fact that CT requires more than 180° of projections to formulate a reconstructed image. Given various limitations encountered in the commercially available scanners, the amount of time required to collect a complete set of projections is significant as compared to the patient motion. For illustration, lets consider the imaging of a heart. Cardiac CT is typically performed with the aid of an EKG signal to synchronize the data acquisition and reconstruction with the phase of the cardiac motion. The data needs not only be acquired during the quiescent cardiac period, but also needs to be collected at the same cardiac phase over multiple cardiac cycles. Although EKG gating performs satisfactorily in most cases, there are a significant number of cases in which the gating provided by the EKG is suboptimal. This is mainly due to the fact that EKG represents only the electrical properties of the heart. It is well known that the electrical signal does not truly represent the mechanical state of the heart. In addition, the duration of the quiescent period changes with the patient heart rate. As the heart rate increases, the quiescent period shortens. Therefore, for a scanner with a given rotation speed (e.g., 0.35 s), there is an upper limit on the heart rate in order for EKG-gated CT to function properly. Analysis has shown that the upper limit is around 70 bpm. This represents less than 70% of the patient population. It is desirable to scan patients with higher heart rates. It is also desirable to enable scanners with slow gantry speeds to perform cardiac CT scans.

Earlier, an integrated ultrasound-CT approach was proposed wherein both the ultrasound and CT data are acquired simultaneously during the data acquisition and reconstruction process (see U.S. patent application Ser. No. 11/276,195, titled Combined Ultrasound and CT Device for Motion Compensation). Because the two datasets are acquired at the same time, the information provided by ultrasound on the shape and location of the heart can be used directly to help to combat CT motion artifacts. Below is disclosed a reconstruction algorithm for the motion compensation.

BRIEF DESCRIPTION OF THE INVENTION

In one aspect, a method includes fitting a motion map from a first imaging modality with a first FOV to a second imaging modality different from the first with a second FOV sized differently than the first FOV.

In another aspect, a method includes using a motion vector of a heart wall in a region away from the heart wall.

In still another aspect, a system is provided. The system includes a radiation source configured to emit radiation, a detector positioned to receive the radiation, and a computer coupled to the source and detector. The computer is configured to fit a motion map from a first imaging modality with a first FOV to a second imaging modality different from the first with a second FOV sized differently than the first FOV.

In yet another aspect, a computer readable medium is embedded with a program. The program is configured to instruct a computer to use a motion vector of a heart wall in a region away from the heart wall.

DETAILED DESCRIPTION OF THE INVENTION

Figure 1:
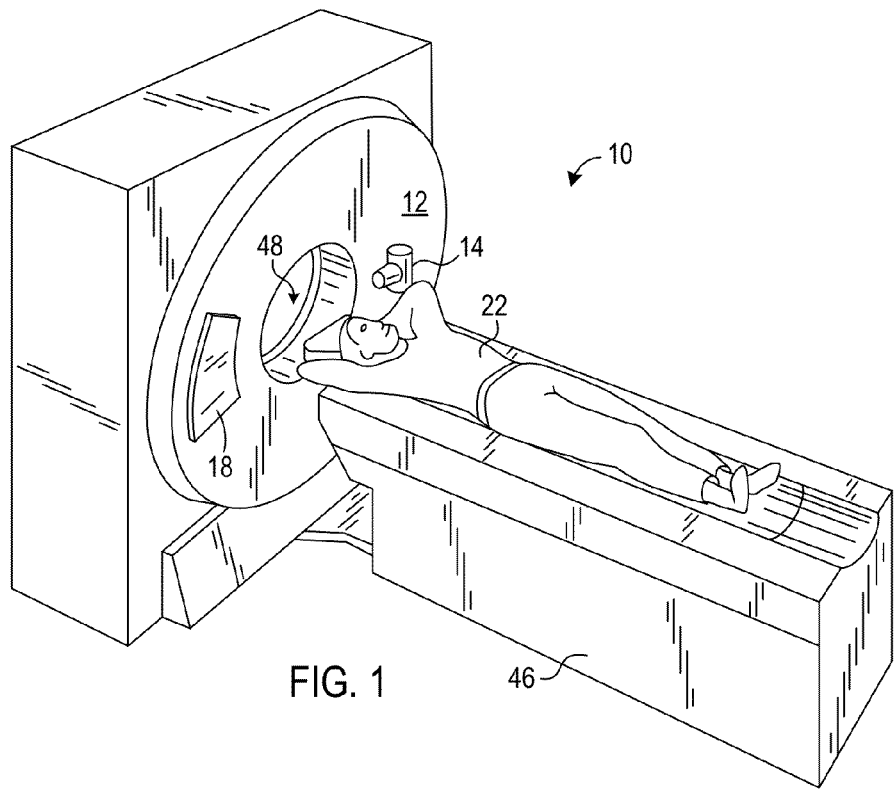
FIG. 1 is a pictorial view of a CT imaging system embodiment.

There are herein provided methods and apparatus useful for imaging systems such as, for example, but not limited to a Computed Tomography (CT) System. The apparatus and methods are illustrated with reference to the figures wherein similar numbers indicate the same elements in all figures. Such figures are intended to be illustrative rather than limiting and are included herewith to facilitate explanation of an exemplary embodiment of the apparatus and methods of the invention.

In some known CT imaging system configurations, a radiation source projects a fan-shaped beam which is collimated to lie within an X-Y plane of a Cartesian coordinate system and generally referred to as an "imaging plane". The radiation beam passes through an object being imaged, such as a patient. The beam, after being attenuated by the object, impinges upon an array of radiation detectors. The intensity of the attenuated radiation beam received at the detector array is dependent upon the attenuation of a radiation beam by the object. Each detector element of the array produces a separate electrical signal that is a measurement of the beam attenuation at the detector location. The attenuation measurements from all the detectors are acquired separately to produce a transmission profile.

In third generation CT systems, the radiation source and the detector array are rotated with a gantry within the imaging plane and around the object to be imaged such that an angle at which the radiation beam intersects the object constantly changes. A group of radiation attenuation measurements, i.e., projection data, from the detector array at one gantry angle is referred to as a "view". A "scan" of the object includes a set of views made at different gantry angles, or view angles, during one revolution of the radiation source and detector.

In an axial scan, the projection data is processed to reconstruct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a display device.

To reduce the total scan time, a "helical" scan may be performed. To perform a "helical" scan, the patient is moved while the data for the prescribed number of slices is acquired. Such a system generates a single helix from a cone beam helical scan. The helix mapped out by the cone beam yields projection data from which images in each prescribed slice may be reconstructed.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. Therefore, as used herein the term, "image," broadly refers to both viewable images and data representing a viewable image. However, many embodiments generate (or are configured to generate) at least one viewable image.

Figure 2:
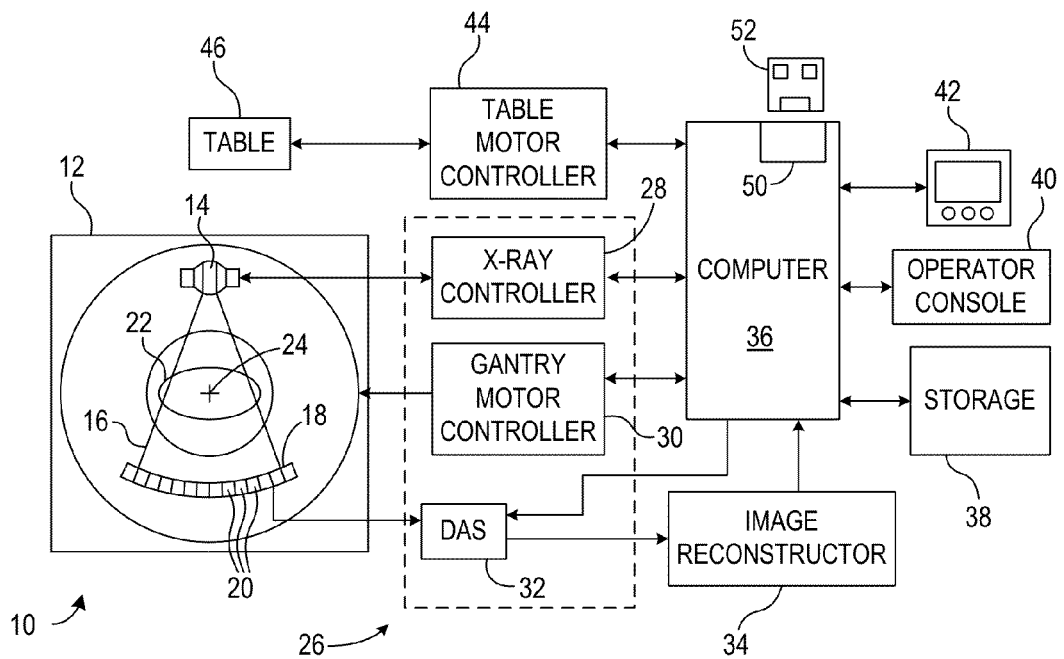
FIG. 2 is a block schematic diagram of the system illustrated in FIG. 1.

FIG. 1 is a pictorial view of a CT imaging system 10. FIG. 2 is a block schematic diagram of system 10 illustrated in FIG. 1. In the exemplary embodiment, a computed tomography (CT) imaging system 10, is shown as including a gantry 12 representative of a "third generation" CT imaging system. Gantry 12 has a radiation source 14 that projects a beam 16 of X-rays toward a detector array 18 on the opposite side of gantry 12. In one embodiment, system 10 is a fused modality system and has the ability to acquire ultrasound data as well as CT data.

Detector array 18 is formed by a plurality of detector rows (not shown in FIGS. 1 and 2) including a plurality of detector elements 20 which together sense the projected X-ray beams that pass through an object, such as a medical patient 22. Each detector element 20 produces an electrical signal that represents the intensity of an impinging radiation beam and hence the attenuation of the beam as it passes through object or patient 22. An imaging system 10 having a multislice detector 18 is capable of providing a plurality of images representative of a volume of object 22. Each image of the plurality of images corresponds to a separate "slice" of the volume. The "thickness" or aperture of the slice is dependent upon the thickness of the detector rows.

During a scan to acquire radiation projection data, gantry 12 and the components mounted thereon rotate about a center of rotation 24. FIG. 2 shows only a single row of detector elements 20 (i.e., a detector row). However, multislice detector array 18 includes a plurality of parallel detector rows of detector elements 20 such that projection data corresponding to a plurality of quasi-parallel or parallel slices can be acquired simultaneously during a scan.

Rotation of gantry 12 and the operation of radiation source 14 are governed by a control mechanism 26 of CT system 10. Control mechanism 26 includes a radiation controller 28 that provides power and timing signals to radiation source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized radiation data from DAS 32 and performs high-speed image reconstruction. The reconstructed image is applied as an input to a computer 36 that stores the image in a mass storage device 38.

Computer 36 also receives commands and scanning parameters from an operator via a console 40 that has a keyboard. An associated cathode ray tube display 42 allows the operator to observe the reconstructed image and other data from computer 36. The operator supplied commands and parameters are used by computer 36 to provide control signals and information to DAS 32, radiation controller 28, and gantry motor controller 30. In addition, computer 36 operates a table motor controller 44 that controls a motorized table 46 to position patient 22 in gantry 12. Particularly, table 46 moves portions of patient 22 through gantry opening 48.

In one embodiment, computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or an other digital source such as a network or the Internet, as well as yet to be developed digital means. In another embodiment, computer 36 executes instructions stored in firmware (not shown). Generally, a processor in at least one of DAS 32, reconstructor 34, and computer 36 shown in FIG. 2 is programmed to execute the processes described below. Of course, the method is not limited to practice in CT system 10 and can be utilized in connection with many other types and variations of imaging systems. In one embodiment, Computer 36 is programmed to perform functions described herein, accordingly, as used herein, the term computer is not limited to just those integrated circuits referred to in the art as computers, but broadly refers to computers, processors, microcontrollers, microcomputers, programmable logic controllers, application specific integrated circuits, and other programmable circuits.

Although the herein described methods are described in a medical setting, it is contemplated that the benefits of the invention accrue to non-medical imaging systems such as those systems typically employed in an industrial setting or a transportation setting, such as, for example, but not limited to, a baggage scanning CT system for an airport or other transportation center. Additionally, although described in a human patient setting it is contemplated that the benefits of the invention accrue to non-human imaging systems such as those used to image animals.

Returning now to the topic of motion compensation. Denote by (x, y, z, t) the coordinate of a reconstruction voxel, (x, y, z), at time t. For the convenience of discussion, one can typically select the reference time t corresponding to the half way point inside the data acquisition window. For the case of a halfscan, for example, the entire data acquisition covers the view range roughly from 0° to 220° for a typical CT geometry (180°+fan angle). The center view angle is then at 110°. At any time t+$\Delta$t, the same pixel is moved to the location (x+$\Delta$x, y+$\Delta$y, z+$\Delta$z, t+$\Delta$t). An algorithm was proposed to map the current voxel location to the reference voxel location during the backprojection process (see C. J. Ritchie, J. D. Godwin, C. R. Crawford, W. Stanford, H. Anno, Y. Kim, "Minimum Scan Speeds for Suppression of Motion Artifacts in CT," Radiology 185(1), pp. 37-42, 1992).

This approach, unfortunately, cannot be applied directly to the Volume CT—ultrasound (VCT-U/S) system due to several major issues. The first is due to the row-wise cone-to-parallel rebinning performed as part of the VCT reconstruction process. For each rebinned projection, the original motion map cannot be used directly since different projection samples are collected at different time windows. The second reason is the mismatch between the VCT scan field-of-view (FOV) and the U/S FOV. In general, the CT FOV is much larger. Therefore, not all voxels inside the CT FOV have proper mapping function produced by the ultrasound device. The third issue is related to the ultrasound image itself. Because of the characteristics of the ultrasound, the motion map is generated only for the soft-tissue regions. The lung region, unfortunately, does not have a valid mapping function provided by the ultrasound device. To overcome these shortcomings, the following algorithm is described.

Figure 3:
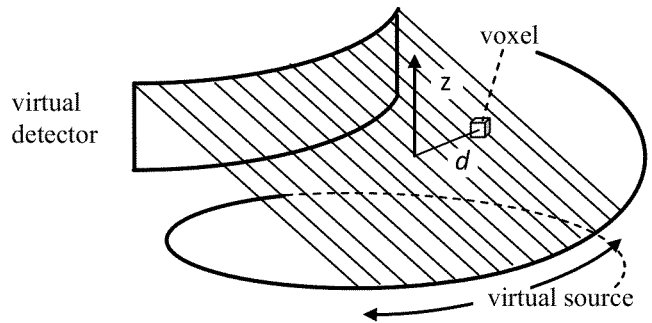
FIG. 3 illustrates a cone beam to parallel rebinning.

To fully understand the algorithm, a brief description of the rebinning process is in order. With cone-parallel rebinning, each parallel view is formed with a virtual detector and a virtual source by combining samples from multiple cone beam projections, as shown in FIG. 3. During the cone-parallel rebinning process, there is a fixed relationship between the distance (d) of a parallel ray to the iso center, and the projection angle (β+Δβ) at which the cone beam sample comes from. Here β is the projection angle of the parallel view. For a ray that passes through a pixel at a distance d from the iso-channel, the angular difference, Δβ, between the iso-ray and the ray-of-interest can be calculated based on:

$$\Delta\beta = -\gamma = -\sin^{-1}\left(\frac{d}{R}\right) \quad (1)$$

where R is the source-to-iso distance and γ is the fan angle from which the original cone beam sample is rebinned. Since in a typical CT scan mode the gantry rotates at a constant speed, the projection angle β scales linearly with time. Therefore, the amount of angular change, Δβ, corresponds to a time change, Δτ:

$$\Delta\tau = \frac{T}{2\pi}\Delta\beta = \frac{-T}{2\pi}\sin^{-1}\left(\frac{d}{R}\right) \quad (2)$$

where T is the periodicity of the gantry rotation. At projection angle β, the distance, d, between the iso-ray and a ray passing through voxel located at (x, y, z) can be calculated by:

$$d = x\cos(\beta) + y\sin(\beta) \quad (3)$$

Combining equations (2) and (3), we have:

$$\Delta\tau = \frac{-T}{2\pi}\sin^{-1}\left(\frac{x\cos(\beta) + y\sin(\beta)}{R}\right) \quad (4)$$

Figure 4:
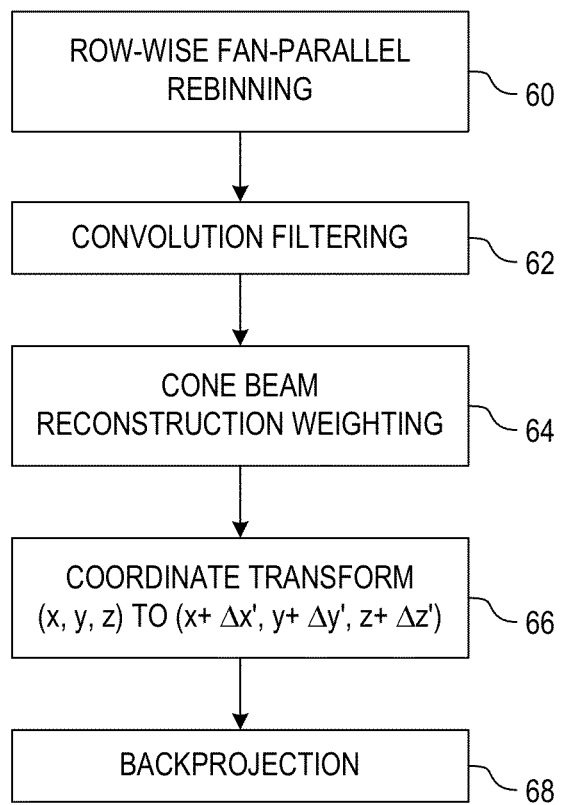
FIG. 4 illustrates the reconstruction process.

Note that the timing change is location-dependent. That is, the amount of voxel location adjustment for a particular rebinning view comes from the motion mapping function generated over a range of time interval. Therefore, for a rebinned projection view with a projection view angle β and is collected at time Δt relative to the reference center view, each voxel in the original reference frame (x, y, z, t) is mapped to a new coordinate (x+Δx', y+Δy', z+Δz', t+Δt+Δτ), where Δx', Δy', and Δz' is the motion at time t+Δt+Δτ. The entire reconstruction process can now be described by the flowchart shown in FIG. 4.

First a row-wise fan-parallel rebinning is done at 60. Then a convolution filtering is done at 62. Then a cone beam reconstruction weighting is done at 64, and a coordinate transform is done at 66. Lastly, a backprojection is done at 68. It should be noted that although the weighting is applied after the convolution filtering step in this figure, it can be applied before the fan-parallel rebinning or after the fan-parallel rebinning (before convolution filtering). Since the reconstruction algorithm itself is not the focus of this study, we will not discuss all other options. For example, the example shown in this figure generally represents filtered backprojection approach. The coordinate transform process can be applied also to iterative reconstruction type of algorithms. That is, the "guessed" reconstructed image is forward projected and compared to the measured projections. Based on the difference, the original image is updated so that the projected view and the measured view match better. This process continues for several iterations until certain criteria is met. The coordinate transform process needs to be applied to both the forward projection as well as the backprojection processes.

Figure 5:
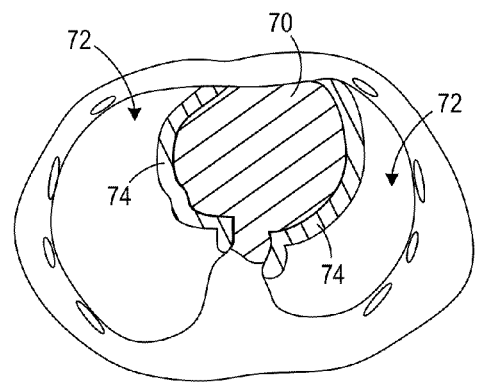
FIG. 5 illustrates different regions or zones.

Now consider the issue of FOV mismatch and missing motion map for the lung region. To address these issues, one needs to consider the characteristics of a cardiac imaging. Since all of the cardiac acquisitions are performed with patient breath-hold, the chest wall motion can be safely ignored. This observation helps to resolve partially the issue of a smaller FOV offered by the ultrasound device. Next, consider the motion in the lung region. Note that the lung region immediately adjacent to the heart exhibits significant motion due to the pushing and pulling of the heart muscles. For the lung regions that are far away from the heart, the motion can be safely assumed to be zero, similar to the assumption made for the chest wall motion, as illustrated in FIG. 5. FIG. 5 illustrates a heart 70, a transition region 74 around the heart, and a region 72 where no motion takes place during the breath-hold. Due to the elasticity of the lung tissue, the motion in between the beating heart and the stationary lung region should be a smoothly varying function. The maximum displacement is at the exterior wall of the heart and gradually reduces to zero some distance away.

The motion map produced by ultrasound can now be extended to the entire FOV using the following method. Denoting by $\vec{\psi}(x,y,z,t)$ the motion vector produced by the ultrasound device for voxel (x, y, z) at time t, by H the heart region, and T the transition region, the motion vector for the entire FOV, $\vec{\eta}(x,y,z,t)$, is then:

$$\vec{\eta}(x, y, z, t) = \begin{cases} \vec{\psi}(x, y, z, t), & (x, y, z) \subset H \\ w(r)\vec{\psi}(x_0, y_0, z_0, t), & (x, y, z) \subset T \\ 0, & \text{otherwise} \end{cases} \quad (5)$$

where r is the distance of point (x, y, z) to the region H, ($x_0$, $y_0$, $z_0$) is the location of the external heart wall, and 0<w(r)<1 is a monotonically decreasing function of r. In other words, moving away from the heart the weights decrease, and once outside the transition region, the motion is deemed non-existent.

Figure 6:
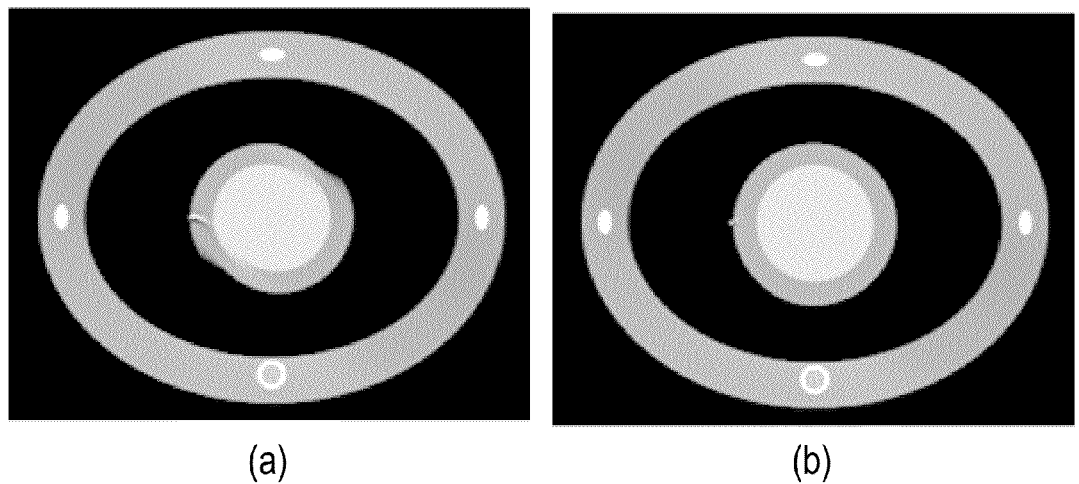
FIG. 6 illustrates the results of the herein described methods and apparatus.

Computer simulations were performed to demonstrate the efficacy of the herein described approach. The phantom consists of two parts: the chest wall and heart. The chest wall is stationary and the heart shrinks and expands at 100 bpm. The linear dimension of the heart at full contraction is 60% of its full relaxation, corresponding to an ejection fraction of 78%. The CT gantry rotation speed is 0.35 s. FIG. 6(a) shows the reconstructed image without any motion compensation. Distortions in the heart region are clearly visible. With the herein described correction algorithm, the reconstructed image is shown in FIG. 6(b). The shape of the heart is nicely restored.

Technical effects of the herein described methods and apparatus include less motion artifacts in reconstructed images.

Exemplary embodiments are described above in detail. The assemblies and methods are not limited to the specific embodiments described herein, but rather, components of each assembly and/or method may be utilized independently and separately from other components described herein.

While the invention has been described in terms of various specific embodiments, those skilled in the art will recognize that the invention can be practiced with modification within the spirit and scope of the claims.

What is claimed is:

1. A system comprising:
a radiation source configured to emit radiation;
a detector positioned to receive the radiation; and
a computer coupled to the source and detector, the computer programmed to:
acquire a first set of imaging data having a first field-of-view (FOV) via the radiation source and detector, the first set of imaging data comprising imaging data of a first object and of a second object;
acquire a first set of motion data of the first object, wherein the first set of motion data comprises motion data of the first object acquired via a first imaging device having an imaging modality different from the modality of the radiation source and detector, and wherein the first set of motion data has a second FOV different from the first FOV;
reconstruct an image, wherein the computer is programmed to:
generate a second set of imaging data based on the first set of imaging data; and
apply a coordinate transform to the second set of imaging data, the coordinate transform comprising motion vector data for voxels of the first object, motion vector data set to zero for voxels of a motion-free region of the second object, and motion vector data for voxels of a transition region of the second object located between the first object and the motion-free region of the second object.

2. The system of claim 1 further comprising:
a rotatable gantry having the radiation source and the gantry mounted thereto;
wherein computer is further programmed to cause rotation of the rotatable gantry;
wherein the first imaging device is an ultrasound device; and
wherein the first FOV is larger than the second FOV.

3. The system of claim 1 wherein the first set of motion data comprises cardiac motion data.

4. The system of claim 1 wherein the computer, in being programmed to generate the second set of imaging data, is programmed to:
apply a row-wise fan-parallel rebinning to imaging data based on the first set of imaging data;
apply a convolution filtering to imaging data based on the first set of imaging data;
apply a cone beam reconstruction weighting to imaging data based on the first set of imaging data; and
apply a backprojection to imaging data based on the first set of imaging data.

5. The system of claim 1 wherein the transition region of the second object corresponds to a region of the second object having motion therein caused by the first object.

6. The system of claim 1 wherein the computer, in being programmed to apply the coordinate transform comprising motion vector data for voxels of the transition region, is programmed to apply the coordinate transform comprising a function of motion data that monotonically deceases as a distance within the transition region increases away from the second object.

7. The system of claim 1 wherein the computer, in being programmed to apply the coordinate transform, is programmed to apply a coordinate transform given by:

$$\vec{\eta}(x, y, z, t) = \begin{cases} \vec{\psi}(x, y, z, t), & (x, y, z) \subset H \\ w(r)\vec{\psi}(x_0, y_0, z_0, t), & (x, y, z) \subset T \\ 0, & \text{otherwise} \end{cases}$$

where H is a heart region, T is the transition region, r is the distance of point (x, y, z) to the region H, (x0, y0, z0) is the location of an external wall of a heart, and 0<w(r)<1 is a monotonically deceasing function of r.

8. A method comprising:
obtaining a first set of imaging data comprising imaging data of a first object and of a second object acquired via a first imaging device having a first imaging modality, wherein the first set of imaging data has a first field-of-view (FOV);
obtaining a first set of motion data of the first object, wherein the first set of motion data comprises motion data of the first object acquired via a second imaging device having a second imaging modality different from the first imaging modality, and wherein the first set of motion data has a second FOV different from the first FOV;
generating an image based on an application of motion data from the first set of motion data to imaging data based on the first set of imaging data, wherein generating the image comprises applying a coordinate transform to imaging data that are based on the first set of imaging data; and
wherein applying the coordinate transform comprises applying a coordinate transform comprising motion vector data for voxels of the first object, motion vector data set to zero for voxels of a motion-free region of the second object, and motion vector data for voxels of a transition region of the second object, the transition region located between the first object and the motion-free region.

9. The method of claim 8 further comprising:
obtaining the first set of imaging data via a CT imaging device; and
obtaining the first set of motion data via an ultrasound imaging device, wherein the second FOV is smaller than the first FOV.

10. The method of claim 9 further comprising simultaneously obtaining the first set of imaging data and the first set of motion data.

11. The method of claim 8 wherein obtaining the first set of imaging data comprises obtaining a first set of cardiac imaging data, and wherein obtaining the first set of motion data comprises obtaining a first set of cardiac motion data.

12. The method of claim 8 wherein generating the image further comprises:
applying a row-wise fan-parallel rebinning to imaging data that are based on the first set of imaging data;
applying a convolution filtering to imaging data that are based on the first set of imaging data;
applying a cone beam reconstruction weighting to imaging data that are based on the first set of imaging data; and
applying a backprojection to imaging data that are based on the first set of imaging data.

13. The method of claim 12 wherein obtaining the first set of imaging data comprises obtaining imaging data of a heart and of a lung, wherein the heart corresponds to the first object and the lung corresponds to the second object.

14. The method of claim 8 wherein applying the coordinate transform comprising motion vector data for voxels of the transition region comprises applying the coordinate transform comprising a function of motion data that monotonically deceases as a distance within the transition region increases away from the heart.

15. The method of claim 8 wherein the applying the coordinate transform comprises applying a coordinate transform given by:

$$\vec{\eta}(x, y, z, t) = \begin{cases} \vec{\psi}(x, y, z, t), & (x, y, z) \subset H \\ w(r)\vec{\psi}(x_0, y_0, z_0, t), & (x, y, z) \subset T \\ 0, & \text{otherwise} \end{cases}$$

where H is a heart region, T is the transition region, r is the distance of point (x, y, z) to the region H, (x0, y0, z0) is the location of an external wall of a heart, and 0<w(r)<1 is a monotonically deceasing function of r.

16. A computer readable storage medium having stored thereon a set of instructions, which, when executed by one or more processors, causes the one or more processors to:
acquire a first set of imaging data having a first field-of-view (FOV), the first set of imaging data comprising imaging data of an object acquired via a first imaging device;
acquire a first set of motion data having a second FOV different from the first FOV, wherein the first set of motion data comprises motion data of the object generated via a second imaging device having an imaging modality different from an imaging modality of the first device; and
reconstruct an image based on an application of motion data from the first set of motion data to imaging data based on the first set of imaging data; wherein the set of instructions that cause the one or more processors to reconstruct the image, cause the one or more processors to:
apply a cone beam reconstruction weighting to imaging data that are based on the first set of imaging data;
apply a row-wise fan-parallel rebinning to imaging data that are based on the first set of imaging data;
apply a convolution filtering to imaging data that are based on the first set of imaging data;
apply a coordinate transform to imaging data that are based on the first set of imaging data; and
apply a backprojection to imaging data that are based on the first set of imaging data; and
wherein the set of instructions that cause the one or more processors to apply the coordinate transform, cause the one or more processors to apply a coordinate transform comprising motion vector data for voxels of a heart, motion vector data set to zero for voxels of a motion-free region, and motion vector data for voxels of a transition region located between the heart and the motion-free region.

17. The computer readable storage medium of claim 16 wherein the imaging modality of the first device is CT, wherein the imaging modality of the second device is ultrasound, and wherein the second FOV is smaller than the first FOV.

18. The computer readable storage medium of claim 16 wherein the first set of imaging data comprises cardiac imaging data, and wherein the first set of motion data comprises cardiac motion data.

19. The computer readable storage medium of claim 16 wherein the set of instructions that cause the one or more processors to apply the coordinate transform, cause the one or more processors to apply a coordinate transform given by:

$$\vec{\eta}(x, y, z, t) = \begin{cases} \vec{\psi}(x, y, z, t), & (x, y, z) \subset H \\ w(r)\vec{\psi}(x_0, y_0, z_0, t), & (x, y, z) \subset T \\ 0, & \text{otherwise} \end{cases}$$

where H is a heart region, T is the transition region, r is the distance of point (x, y, z) to the region H, (x0, y0, z0) is the location of an external wall of a heart, and 0<w(r)<1 is a monotonically deceasing function of r.

* * * * *